United States Patent [19]

Bourinbaiar

[11] Patent Number: 6,001,808
[45] Date of Patent: Dec. 14, 1999

[54] METHOD OF TREATING HERPES VIRUS INFECTIONS WITH SPERMOSTATIC GRAMICIDIN

[75] Inventor: Aldar S. Bourinbaiar, New York, N.Y.

[73] Assignee: Metatron, Inc., Bayshore, N.Y.

[21] Appl. No.: 08/912,113

[22] Filed: Aug. 15, 1997

Related U.S. Application Data

[60] Provisional application No. 60/024,134, Aug. 19, 1996.
[51] Int. Cl.$^6$ .................................................. A61K 38/00
[52] U.S. Cl. ................................................................ 514/14
[58] Field of Search .................................................. 514/14

[56] References Cited

U.S. PATENT DOCUMENTS 5,552,382  9/1996  Bourinbaiar .............................. 514/14

OTHER PUBLICATIONS

Bourinbaiar et al., Arch. Virol., 142 (11), 2225–2235, Abstract Only, 1997.

Lee et al, J. Pharm. Sci., 85(1), 91–5 Abstract Only, 1996.

*Primary Examiner*—Jerome D. Goldberg
*Attorney, Agent, or Firm*—Henry D. Coleman; R. Neil Sudol

[57] ABSTRACT

The present invention relates to a method of using antibiotic gramicidin for the therapy and prevention of herpes virus infections. Gramicidin is also useful in suppressing sperm motility without affecting its viability and may thus be used as an active ingredient of topical contraceptive formulations either alone or in combination with chelating agents such as EDTA or salts thereof.

11 Claims, 5 Drawing Sheets

METHOD OF TREATING HERPES VIRUS INFECTIONS WITH SPERMOSTATIC GRAMICIDIN

RELATED APPLICATION

This application derives benefit from provisional application Ser. No. 60/024,134, filed Aug. 19, 1996.

FIELD OF THE INVENTION

This invention relates to a method of preventing and treating herpes virus infections with gramicidin. This invention also relates to a method of preventing conception by inhibiting sperm motility with low non-spermicidal doses of pharmaceutical composition containing gramicidin alone or in combination with chelating agents such as EDTA.

BACKGROUND OF THE INVENTION

Herpes viruses are DNA viruses and among them are herpes simplex virus type 1 (HSV-1), herpes simplex virus type 2 (HSV-2), varicella-zoster virus (VZV), cytomegalovirus (CMV), Epstein-Barr virus (EBV), and various other human herpes viruses (HHV) such as HHV-6, HHV-7, and HHV-8. Herpes viruses are in general transmitted by person-to-person contact by infected body secretions. The infection by said viruses can cause various diseases in humans. The severity of infection depends on the virus type and can sometimes be relatively mild, but under certain circumstances can be fatal to the host.

For example, symptomatic HSV-1 infections are fairly benign in immunocompetent individuals as HSV-caused oropharyngeal sores tend to disappear spontaneously. Primary clinical manifestations of HSV-2 infection, which is mainly transmitted sexually, are anogenital lesions. Genital herpes affects one third of the world's population, and among people with human immunodeficiency virus (HIV) the incidence may be as high as 80 percent. HSV infections are particularly severe and even life-threatening to patients with acquired immune deficiency syndrome (AIDS). Only 20 percent of herpes seropositive persons have symptomatic infection. The rest of them are asymptomatic but nevertheless are able to shed the virus. In view of the high prevalence of genital herpes and its cofactor role in enhancing sex-borne HIV transmission the herpesviruses are of particular concern. Cytomegalovirus may cause eye infection which may result in blindness if left untreated. Varicella-zoster virus may cause dermatomal vesicular rash or shingles that can be quite painful. Other herpes viruses such HHV-8 were recently implicated to cause malignant diseases in humans such as lymphomas and Kaposi's sarcoma-tumors that are frequently found in persons infected with HIV. The presence of such tumors is comprised in the clinical definition of acquired immunodeficiency syndrome (AIDS)—a fatal clinical condition that is commonly associated with HIV infection.

Herpes virus infections are usually treated with nucleoside analogs such as acyclovir (ACV). Although ACV is relatively safe and non-toxic, its prophylactic use to suppress HSV shedding in the genital Although ACV is relatively safe and non-toxic, its prophylactic use to suppress HSV shedding in the genital tract would require repeated exposure to the drug and may thus favor the spread of drug-resistant strains. The need for alternative agents effective against ACV-resistant mutants and which can be used topically for prophylaxis of HSV is obvious. Ideally, one must identify an effective and safe compound that could afford barrier protection against herpesviruses in general and against HSV in particular.

It would also be preferable if such an agent were also useful against common microbial sexually transmitted diseases (STDs) and played a contraceptive role as well. As ACV is not suitable for these purposes alternative, multifunctional agents are needed. Nonoxynol-9 (N9), the most common spermicidal ingredient in topical vaginal formulations, initially appeared to fulfill this requirement. However, several lines of evidence exist indicating that N9 is less effective and more toxic than assumed originally.

Linear gramicidin or gramicidin D is an antibiotic first discovered in 1939 by Rene Dubos and has broad spectrum activity against gram-positive bacteria, fungi, and protozoa. Commercial gramicidin D preparation consists of a mixture of three pairs of gramicidins A, B, and C, making up approximately 80%, 6%, and 14% respectively. Each pair consists of 2 subspecies, one with valine in position one, comprising 80–95% of the component, and the other with isoleucine. Gramicidin does not irritate mucous membranes, is poorly absorbed through the skin, and it is still used today as one of the active ingredients in ophthalmic antimicrobial solutions, e.g., Neosporin. Gramicidin belongs to the porin type of antibiotics and acts by forming cation channels across the cell membrane which results in potassium efflux. Gramicidin has been used for over fifty years mainly as a broad spectrum topical antimicrobial, antifungal, and anti-protozoan agent. Cyclic or gramicidin S is used in the former Soviet Union (FSU) as an active ingredient of a spermicidal vaginal contraceptive and as antimicrobial agent. Gramicidin S is unrelated to gramicidin D as these two antiobiotics have different chemical structure and mode of action. Gramicidin S is a detergent and acts by lysing cell membranes in a manner similar to N9 detergent. The term "gramicidin" as used herein relates to the linear form of gramicidin. Gramicidin has been recently identified by this inventor as a potent anti-HIV agent as described in the U.S. Pat. No. 5,552,382 relating to the method of prevention of HIV infection. Gramicidin at 10 ng/ml concentration was active not only against lab strains of HIV but also against clinical isolates. However, the use of gramicidin against herpes viruses was not obvious as HIV and herpes viruses are not related genetically and replicate by completely different mechanisms. Thus, while the utility of gramicidin as an anti-HIV agent was known in the prior art, the utility of gramicidin as an anti-herpes agent was totally unpredictable.

SUMMARY OF THE INVENTION

The present invention is based on unexpected discovery that gramicidin displays potent anti-herpes activity at pharmacologically acceptable non-toxic concentrations. The concentrations of gramicidin required to inhibit herpes virus replication and spread are almost identical to those displayed by acyclovir. Furthermore, gramicidin effectively suppresses the replication of herpes virus strains that became resistant to acyclovir treatment. Thus, as acyclovir is used in vivo to treat and prevent herpes virus infections, gramicidin also functions as an anti-herpes agent.

Thus, the present invention provides the method of treating and preventing herpes virus infections such as herpes simplex virus type 1 (HSV-1), herpes simplex virus type 2 (HSV-2), varicella-zoster virus (VZV), cytomegalovirus (CMV), Epstein-Barr virus (EBV), and various other human herpes viruses (HHV) such as HHV-6, HHV-7, and HHV-8. The method comprises administering (topically, intravaginally or rectally) an anti-viral effective amount of gramcidin to an individual suffering from or being exposed to one or more of the above-described viruses. The present invention also relates to a method to prevent the transmission of the abovementioned viruses during sexual intercourse comprising administering an anti-viral effective amount of gramicidin to a person at risk for being exposed to one or more of the above described viruses.

The present invention also includes the pharmaceutical composition consisting of substantially pure gramicidin in combination with a suitable carrier such as cream, solution, lubricant, or gel and containing other ingredients such as chelating agents, e.g., EDTA and salts thereof, or other chemical additives that may enhance the antiviral activity and efficacy.

In a further aspect, gramicidin alone or in combination with such additives can also be used as a contraceptive agent by immobilizing the sperm motility and suppressing sperm penetration across vaginal or cervical mucosa.

In another aspect gramicidin alone or in combination with such additives can also be used as an anti-STD agent. Many microbial STDs such as gonorrhea, syphilis, chlamydia, candidiasis, bacterial vaginosis, and trichomoniasis can cause genital ulcers and inflammations which may facilitate the transmission of herpes viruses that are spread by sexual contact.

Other advantages and features of the invention will be apparent from the following description of the preferred embodiment thereof and appended claims.

DETAILED DESCRIPTION OF THE DRAWINGS

DETAILED DESCRIPTION OF THE INVENTION

The present invention relates to a method for treating or preventing herpes virus infections such as herpes simplex virus type 1 (HSV-1), herpes simplex virus type 2 (HSV-2), varicella-zoster virus (VZV), cytomegalovirus (CMV), Epstein-Barr virus (EBV), and various other human herpes viruses (HHV) such as HHV-6, HHV-7, and HHV-8, which method comprises administering to a patient suffering from a viral infection or at risk for contracting a viral infection an anti-viral effective amount of gramcidin to treat or prevent the viral infection in the patient. In the present method, gramicidin is applied to a virus-affected body part in an anti-virus effective amount.

The term "virus-affected body part" refers to an area of the body where lesions or other manifestations of the virus occur, generally, in the genital area, or on the face, including the eyes and lips. The affected body parts may include, for example, sexual organs, numerous membranes, the skin or other areas of the body where the virus has an effect which can be treated by topical application. The present method is effective even when treating herpes viral infections which are resistant to acyclovir or anti-herpes nucleoside agents.

The term "anti-viral effective amount" is used throughout the specification to describe an amount of gramicidin which inhibits the growth, replication and/or elaboration of the virus in the patient or, in the case of prophylactic methods, prevents the infection in the host (patient) in the first instance.

The term "patient" refers to an animal, generally a human who can be infected with a herpes virus and suffer from the manifestations of herpes viral infection. The patient may be a human or other animal, depending upon the type of virus Primary and recurrent herpes virus-caused lesions can be treated with a simple topical therapy comprising administering an inhibitory effective amount or dose of gramicidin to a human suffering from a herpes infection. The area to be treated may include, for example, the lips, mouth and genital areas and other areas accessible to topical administration which may be the site of a herpes lesion or sore. Thus, the present method relates to the use of effective concentrations or amounts of gramicidin to treat HSV 1 and 2 infections by exposing the virus to anti-HSV effective concentrations of gramicidin. The present method also relates to the use of effective concentrations or amounts of gramicidin to treat other human herpes virus infections by exposing the virus to effective amounts (concentrations) of gramicidin. Pharmaceutical compositions are also an aspect of the present invention as is a method for prophylactically treating or preventing a herpes viral, especially an HSV infection using these compositions. Effective concentrations of gramicidin for treating and/or preventing herpes viral and in particular, HSV infections according to the present invention fall within the range of about 10 ng/ml to about 25 mcg/ml or more (e.g. 50 mcg/ml or more), more preferably from about 100 ng/ml to about 10 mg/ml administered topically, rectally or intravaginally as a solution, cream, gel, ointment or other topically admininistrable form.

Gramicidin may be used both as an an herpes agent (especially an anti-HSV agent) and as a contraceptive agent. For the purpose of guidance it is preferable that if gramicidin is used alone both for preventing herpes virus infection and conception by topically applied preparations the doses of gramicidin attained locally should be in the range between 10 ng and 100 mcg. Due to the dilution factor and "wearing off" of gramicidin in the course of time, the actual formulation may contain up to 100 times more of the active agent than the upper limit attained locally. Thus, the pharmaceutical formulation containing gramicidin may contain up to 10% of said agent or at least 10 mg/ml or at least 10 mg/gram of the pharmaceutical vehicle such as a solution, cream, ointment, lubricant, or gel.

In certain aspects of the present invention, especially including contraceptive aspects, when gramicidin is intended to be used in combination with a chelating agent such as EDTA or salts thereof, the actual concentration of gramicidin may be reduced 100 times and the pharmaceutical formulation may contain at least about 10 mcg/ml up to about 0.1% by weight of the final formulation of EDTA or its salt within the pharmaceutical vehicle. Depending on the intended use being either anti-viral or contraceptive the formulation, the mode of delivery, and the content of gramicidin may be modified to suit the particular needs and requirements according to the well known principles of the art. However, the same formulation can be used for both purposes, if needed.

To prepare the topical pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a topical dose, as a solution, cream, ointment, gel, salve or other topical vehicle, including a sponge, suppository or a related vehicle for intravaginal or intrarectal delivery of gramicidin. A carrier may take a wide variety of forms depending on the form of preparation desired for topical administration, which administration includes intrarectal and intravaginal administration. In preparing pharmaceutical compositions in topical dosage form, any of the usual pharmaceutical media may be used. If desired, the topical delivery vehicle may be sustained release by standard techniques.

The compounds according to the present invention also may advantageously be employed prophylactically to prevent infection or to prevent the occurrence of clinical symptoms associated with the viral infection. Thus, the present invention also encompasses methods for the prevention or prophylactic treatment of herpes viral infections. This prophylactic method comprises administering to a patient in need of such treatment an amount of a compound according to the present invention effective for alleviating, and/or preventing the viral infection.

The effect of gramicidin on the replication of herpes simplex viruses (HSV) type 1 and 2 has been examined and compared to the effect of acyclovir—the nucleoside analog used in the prior art for the therapy of herpes virus infections. Human WI-38 fibroblasts were inoculated with either type of HSV in the presence of serial dilutions of gramicidin (10–0.001 mcg/ml) and reduction in viral yield was measured at 24 hours by ELISA. The low doses of gramicidin (IC50 0.1–0.4 mcg/ml) were shown to be effective against both HSV type 1 and 2. The average 50% inhibitory dose (IC50) of gramicidin against 3 HSV-1 and 4 HSV-2 solates was equal to 0.3 mcg/ml and was similar to the efficacy of the anti-HSV agent acyclovir (ACV). The IC50 of a single dose of gramicidin required to protect WI-38 from cytolytic effect of HSV was 10 mcg/ml at day 5 postinfection. Importantly, gramicidin suppressed the replication of ACV-resistant thymidine kinase and polymerase HSV mutants at doses effective against ACV-sensitive strains.

EXAMPLE 1

Gramicidin was purchased from Sigma (St Louis, Mo.) dissolved in 95% ethanol at concentration 1 mg/ml as a stock solution and kept at room temperature until used. Acyclovir, [2-hydroxyethoxymethyl]guanine (ACV), used as a reference drug, was obtained from Sigma and prepared in saline as 1 mg/ml stock solution.

Human embryonic lung fibroblasts WI-38 (CCL-75, ATCC, Rockville, Md.) were grown in RPMI medium 1640 with 10% FBS, L-glutamine, and penicillin/streptomycin (GIBCO, Grand Island, N.Y.) at 37° C. with 5% $CO_2$ air atmosphere. Herpes viruses that were tested for susceptibility to gramicidin are own in Table 1.

TABLE 1

| | $IC_{50}$ values of gramicidin and acyclovir (ACV) as established by HSV antigen ELISA | | | | |
|---|---|---|---|---|---|
| HSV | | | | $IC_{50}$ (µg/ml) | |
| No. | type | Strain | Phenotype | Gramicidin | Acyclovir |
| 1 | 1 | KOS | ACV-sensitive | 0.2 | 0.4 |
| 2 | 1 | PAAr | Polymerase⁻ | 0.4 | 52.4 |
| 3 | 1 | DM2.1 | TK⁻ | 0.3 | 77.3 |
| 4 | 2 | VR-734 | ACV-sensitive | 0.3 | 0.2 |
| 5 | 2 | 186 | ACV-sensitive | 0.1 | 0.1 |
| 6 | 2 | Kost | TK altered | 0.2 | 15.8 |
| 7 | 2 | 8708 | TK altered | 0.3 | 9.9 |

Most of these viruses are well characterized mutants with deletion or alteration of thymidine kinase (TK) or alteration in DNA polymerase and have been described in detail in the literature. For example, DM2.1 is a TK-deficient HSV-1 mutant. PAAr is a ACV resistant polymerase deficient HSV-.KOS and 186 are ACV-sensitive laboratory controls of HSV type 1 and 2 respectively.

One day prior to the assay WI-38 monolayers were trypsinized with 0.25% trypsin/EDTA (Sigma) and plated in 96-well microculture plates at seeding concentration $10^5$ cells per well. The next day triplicate wells of WI-38 monolayers were exposed to serial 10-fold dilutions (range 10 mcg/ml-1 ng/ml) of gramicidin or ACV. Positive control wells and drug-exposed wells containing 180 mcl of medium received 20 mcl ahquots of HSV-1 or HSV-2 preparation at 5,000 $TCID_{50}$ per well and were incubated further for 24 hours. Thereupon, the supernatants from infected WI-38 fibroblasts were collected and levels of HSV antigen were examined by ELISA (Premier™ HSV, Meridian Diagnostics Inc., Cincinnati, Ohio) according to the manufacturer's instructions. The primary antibody supplied with this ELISA kit recognizes HSV antigens of both virus types. The amount of HSV antigen, corresponding to levels in the inoculum, was subtracted as a blank value from experimental values reached upon virus propagation in host WI-38 cells. IC50 doses were estimated from dose-response curves plotted as a function of log concentrations of drugs.

Inoculated WI-38 cells were grown in the presence of ten-fold dilutions of gramicidin or ACV for five days until all untreated control cells were dead as a result of lytic HSV infection. The culture wells were then exposed for 4 hours to MTS tetrasolium salt and phenazine methosulfate preparation (Cell Titer$^{96}$, Promega, Madison, Wis.) and the optical density of formazan dye was measured in a plate reader at 450 nm with reference filter at 620 nm. The obtained values were then compared to both the absorbance values of dead cells and optical density of uninfected viable cells grown in the same plate. The percent of surviving WI-38 cells in drug-protected cultures was determined from dose-response curves as a function of log concentrations of test drugs.

The effect of test compounds on cell viability was measured by two colorimetric assays as follows. WI-38 cells were grown in the presence or absence of ten-fold dilutions of gramicidin or ACV for two days. The cells were then exposed to MTS/phenazine methosulfate as described above. The conditions for the second, lactate dehydrogenase (LDH) assay, were similar to the MTS test except that a different cell viability parameter was measured. This assay quantitatively measures the stable cytosolic enzyme, LDH, that is released upon cell lysis in much the same way as $^{51}$Cr is released in radioactive assays. The results were evaluated using an enzymatic assay which measures the conversion of INT tetrazolium salt into red formazan product (CytoTox$^{96}$, Promega, Madison, Wis.). A standard 96-well plate reader was set to record wavelength absorbance at 490 nm. The residual LDH activity present in incubation medium was subtracted as a blank value. The amount of LDH released from drug-exposed cells was compared to untreated and detergent-lysed controls according to the formula provided by the manufacturer.

Figure 1:
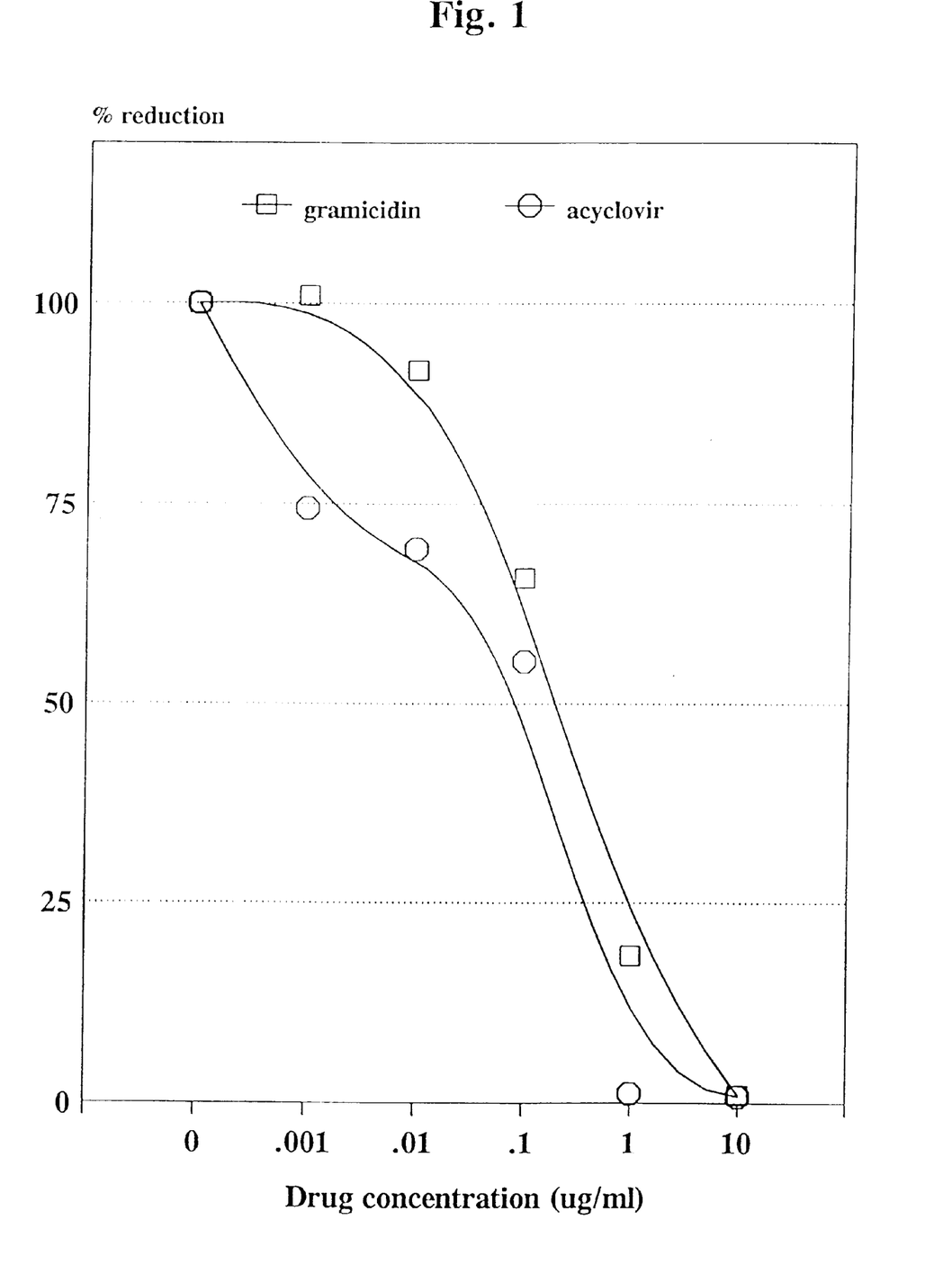
FIG. 1. The effect of gramicidin and acyclovir on herpes simplex virus (HSV) replication in WI-38 cells as measured on day 1 postinfection by antigen ELISA. IC50 values of gramicidin and acyclovir against VR-734 strain of HSV-2 were 0.3 and 0.2 mcg/ml respectively.
Figure 2:
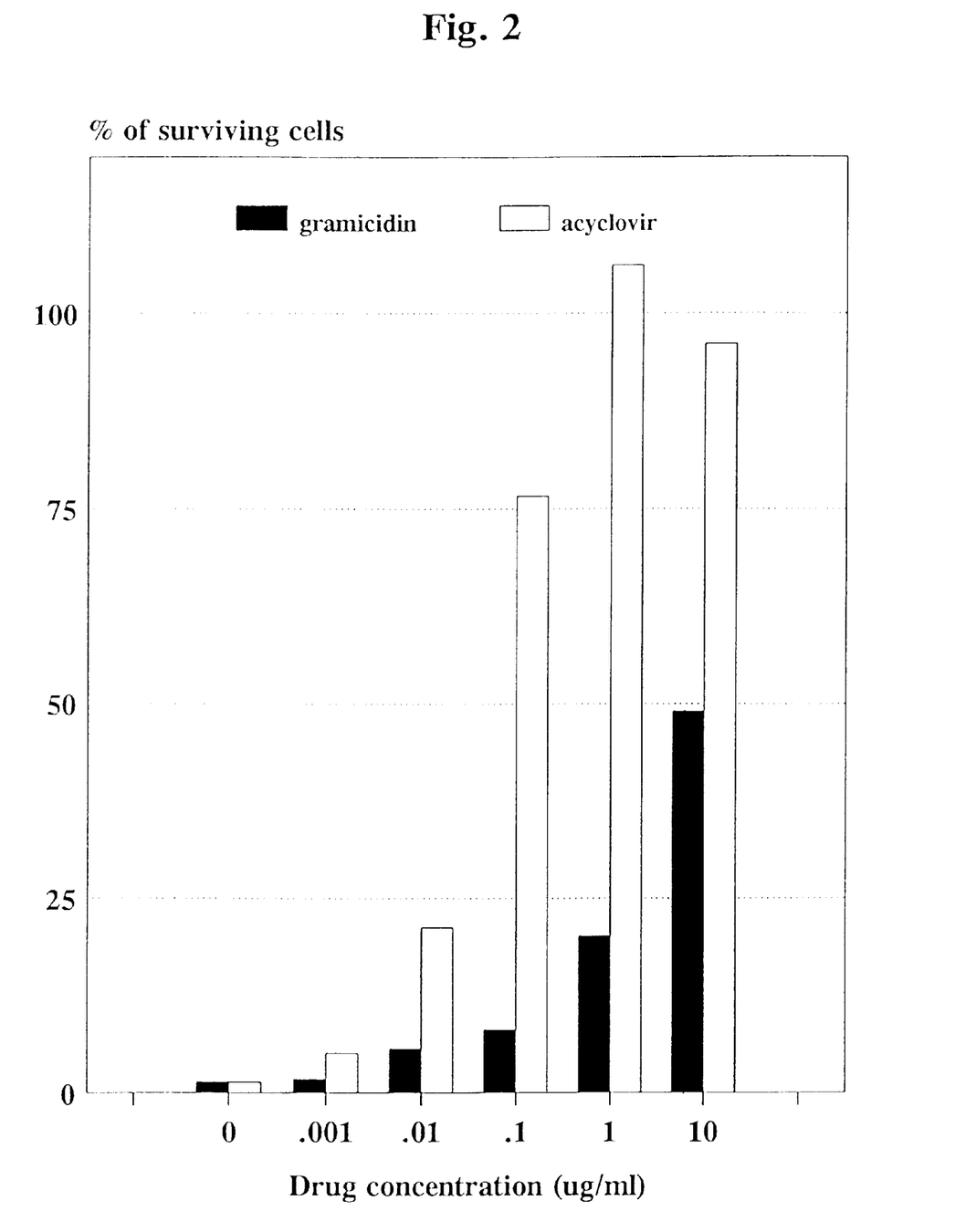
FIG. 2. The protective effect of serial dilutions of gramicidin and acyclovir (shown on the horizontal axis) against cytolytic action of HSV on WI-38 fibroblasts as measured on day 5 postinfection by MTS assay. IC50 values (shown on the left Y axis) of gramicidin and acyclovir against VR-734 strain of HSV-2 were 10 and 0.2 mcg/ml respectively.

As early as 24 hours postinfection HSV-exposed WI-38 fibroblasts displayed typical signs of cytolytic infection characterized by rounding and clumping of dying cells. The severity of infection appeared to be in reverse correlation with the concentration of antivirals present in the well. In order to quantitate this observation the supernatants from infected cultures were collected and assayed by ELISA for HSV antigen. Based on three independent experiments with triplicates for each dose of antivirals it appeared that gramicidin, previously known for anti-HIV and antimicrobial activities, was capable of inhibiting HSV infection. The typical results as illustrated by the effect of antivirals on VR-734 G strain of HSV-2 are shown in FIG. 1. Under described assay conditions the IC50 for gramicidin was 0.3 mcg/ml which was similar to IC50 of ACV tested under identical conditions. However, in virus assays based on measuring the survival of drug-treated fibroblasts, the IC50 of gramicidin was equivalent to 10 mcg/ml (FIG. 2). In ELISA-based tests against four representative ACV-resistant strains the activity of gramicidin was not compromised and appeared to be the same as against ACV-sensitive wild type herpesviruses. ACV-resistant mutants either had deleted (DM2.1) or altered TK (Kost and 8708) or altered viral DNA polymerase (PAAr). The activity of ACV against these strains was significantly weaker (Table 1).

Figure 3:
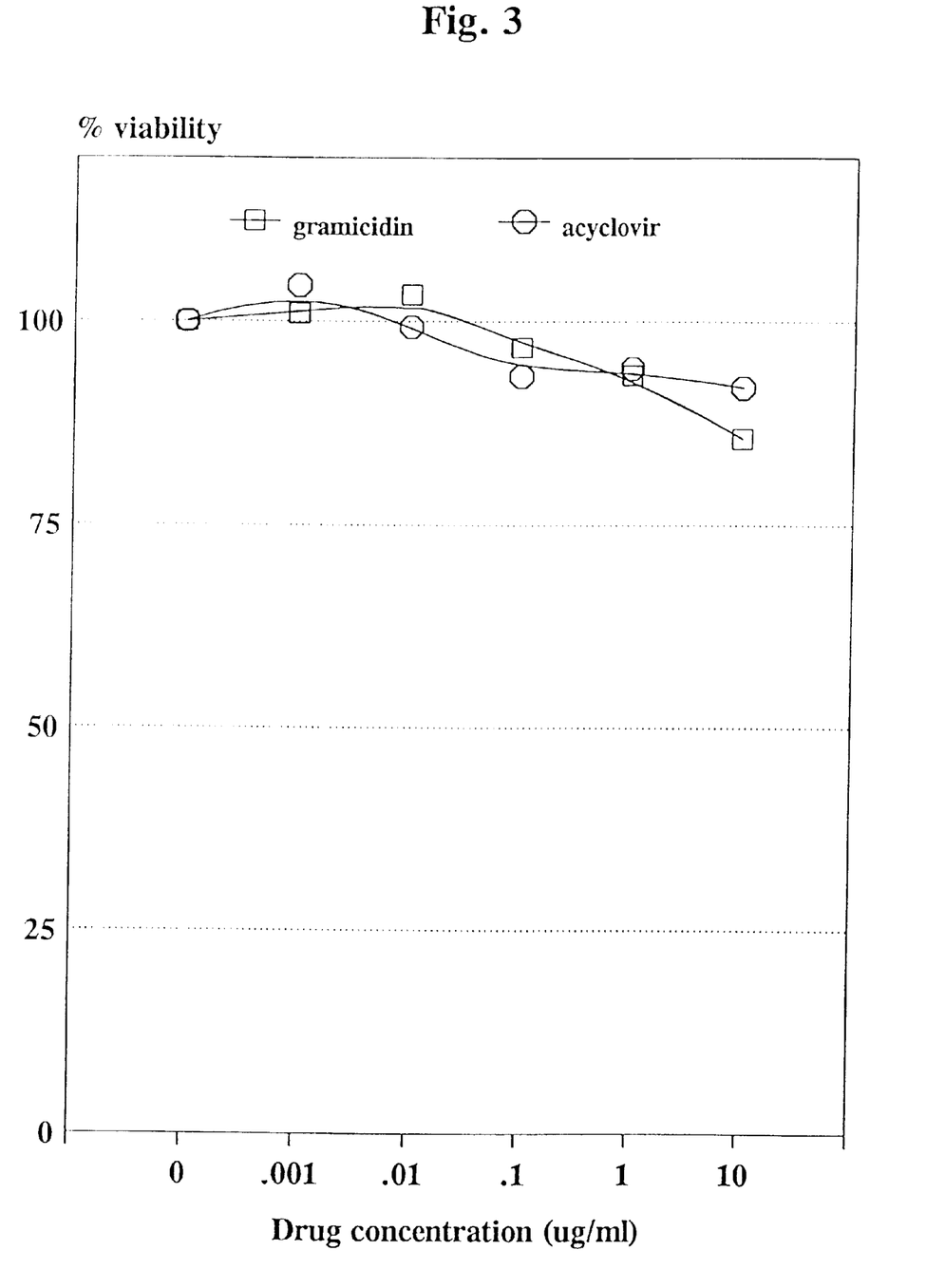
FIG. 3. The effect of gramicidin and acyclovir on viability of WI-38 cells as measured on day 2 by MTS assay. The highest tested 10 mcg/ml dose of each compound had no significant effect in suppressing metabolic activity of host cells.
Figure 4:
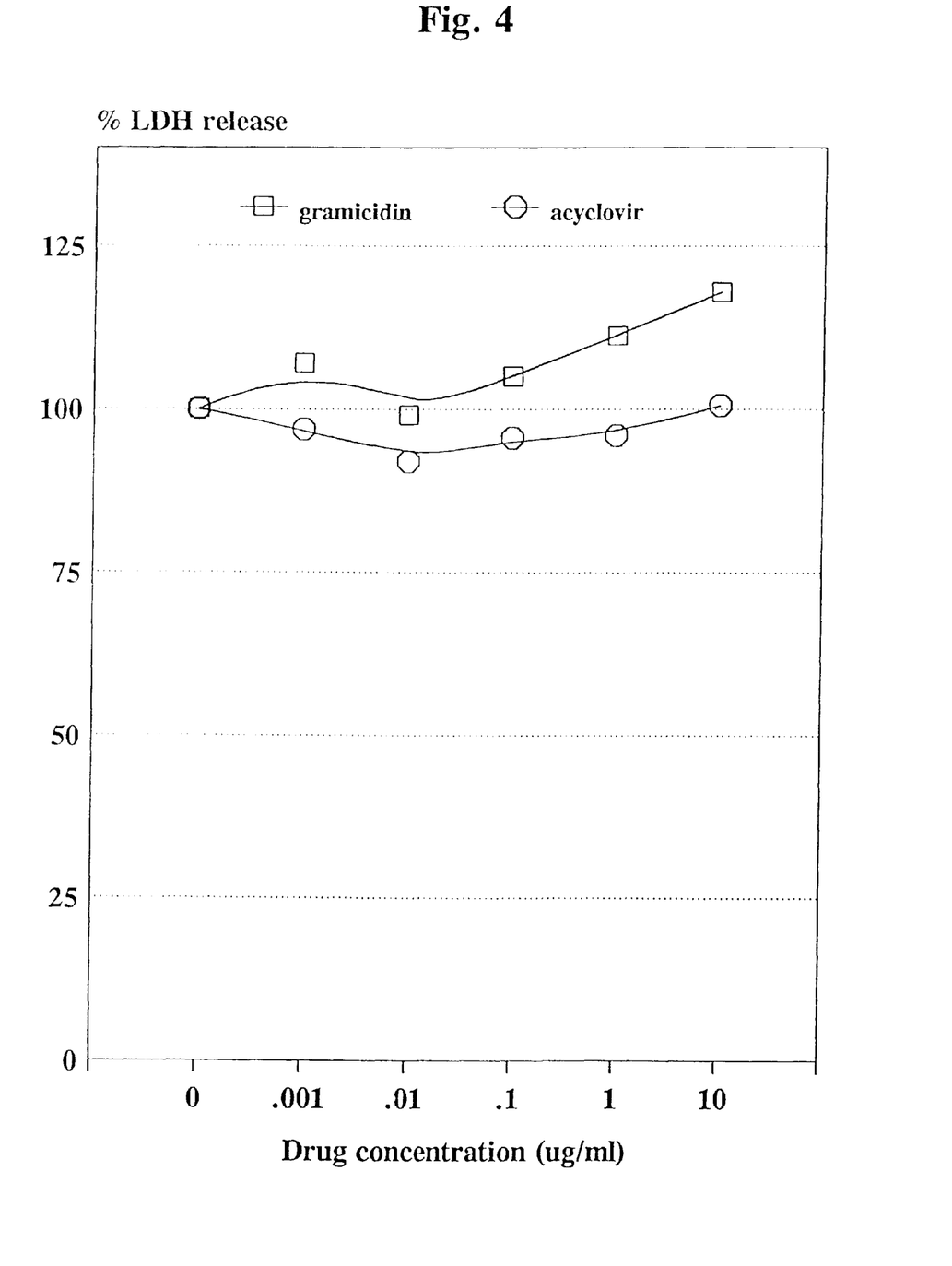
FIG. 4. The effect of gramicidin and acyclovir on LDH release from drug-exposed WI-38 as measured 2 days after the initiation of treatment. The highest levels of excess LDH were within 15% of baseline for untreated controls.
Figure 5:
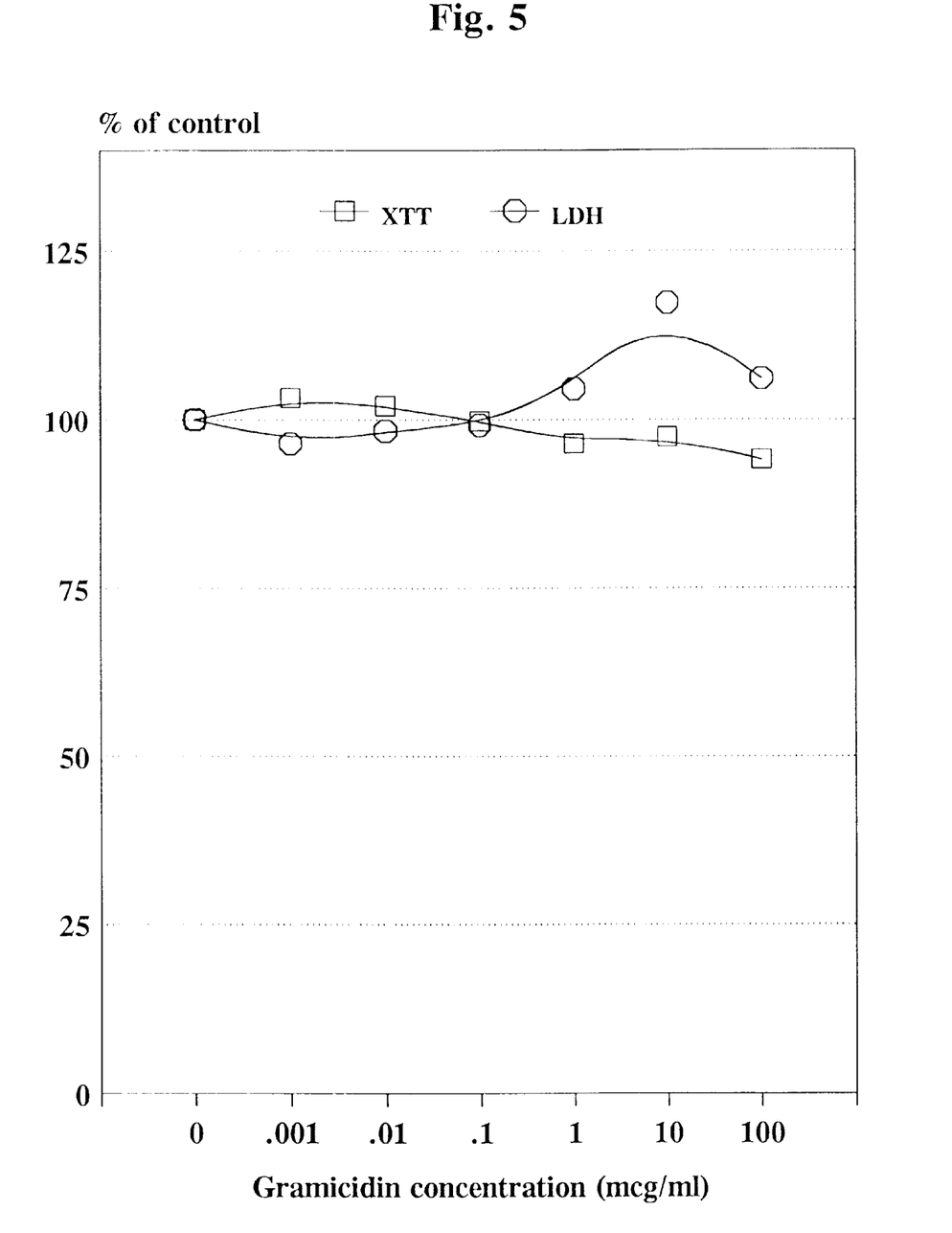
FIG. 5. The effect of serial dilutions of gramicidin (100 mcg–1 ng per ml) on sperm viability as measured by XTT and LDH release assays. Although high doses of gramicidin appeared to enhance LDH release, the effect was negligible. Gramicidin had no effect on mitochondrial hydrogenases even at the highest 100 mcg/ml concentration.

Both drugs, gramicidin and ACV, were not toxic to host WI-38 cells at concentrations that exceeded IC50 by at least two orders of magnitude (FIG. 3). The excess of LDH released from WI-38 cells exposed even to the highest 10 mcg dose of gramicidin was not above 15% baseline of untreated controls, confirming that this compound has low toxicity (FIG. 4).

This example demonstrates that gramicidin is capable of inhibiting HSV replication at concentrations that are comparable to acyclovir. Furthermore, gramicidin has shown better efficacy against ACV-resistant variants with TK or DNA polymerase mutations. MTS and LDH assays revealed that gramicidin was not toxic, which is in agreement with the clinical experience of topical ophthalmic preparations containing 25 mcg/ml of the antibiotic.

The progress in understanding the replication of viruses has yielded a great number of mechanism-based antiviral agents. ACV, vidarabine, ganciclovir, and foscarnet are now routinely used for systemic and topical treatment of HSV infections. AZT-like nucleosides and HIV protease inhibitors are drugs designed for HIV therapy. However, clinical trials revealed an important problem which was particularly alarming among HIV-infected individuals. It became apparent that mutants resistant to current drugs were expanding and replacing sensitive strains in the host population. TK initiates phosphorylation of ACV, and DNA polymerase is inhibited by ACV triphosphate. HSV becomes resistant to ACV due to the loss or mutation of the viral TK enzyme or to the alteration in the viral DNA polymerase. Gramicidin seems to be effective against ACV-resistant HSV and it is unlikely that it targets TK or DNA polymerases.

EXAMPLE 2

Gramicidin S has been and is still used in the former Soviet Union as an over-the-counter spermicidal paste. According to Russian sources, commercial contraceptive formulation contains 0.2% or 2 mg of gramicidin per gram of paste. Approximately 5–6 grams of the spermicide is required to be delivered to the vagina which constitutes a total of 10–12 mg of gramicidin S per application. Gramicidin D, which is unrelated to gramicidin S and which is preferred agent of this invention, has never been used as a spermicide.

In the prior art (U.S. Pat. No. 5,552,382) gramicidin D, by inadvertent analogy with gramicidin S, was suggested as a spermicide. Indeed, gramicidin, when used at 10 mg doses which are similar to doses of gramicidin S it acted as a spermicide, i.e., killed sperm. Unexpectedly, this inventor has discovered that when gramicidin was used at 1,000-fold lower doses it did not kill the sperm but had instead immobilized the movement of the sperm, i.e., acted as a spermostatic agent. Furthermore, when gramicidin was used in combination with 0.1% of EDTA it had the same effect although the effective doses were approximately 1,000,000 times smaller than the original sperm killing 10 mg concentration.

Small doses of gramicidin were compared with a commonly used spermicidal detergent-nonoxynol-9 (N9) for the inhibition of sperm motility, in cervical mucus penetration assay, and by colorimetric tetrazolium salt (MTS) and lactate dehydrogenase (LDH) release assays for testing the toxicity of drugs. Unlike N9, gramicidin did not killed the sperm as the viability of spermatozoa was not significantly affected in the presence of gramicidin. The effective 100% inhibitory concentration (IC100) of gramicidin in a 2-minute sperm immobilization assay was equal to 4 mcg/ml, whereas IC100 of N9 was equal to 200 mcg/ml. This indicates that gramicidin is 50 times more potent than N9. Surprisingly, the addition of 0.1% of chelating agent, EDTA, reduced IC100 of gramicidin to 10 ng/ml, while less than a two-fold enhancement in N9 activity was observed upon combination with EDTA. Likewise, the gramicidin/EDTA combination was 100,000 times more potent than N9/EDTA in the sperm penetration assay. EDTA or related polyaminocarboxylic acids such as EGTA and salts thereof have been reported to affect adversely sperm motility. However, the activity of EDTA alone is not highly specific since it requires very high doses (as shown in Tables 2 and 3).

Gramicidin D and sodium salt of ethylenediaminetetraacetic acid (EDTA) were purchased from Sigma (St Louis, Mo.). The non-ionic detergent, nonoxynol-9 (Igepal CO 630) was obtained from Rhone Poulenc Inc., (Cranberry, N.J.). All reagents were dissolved in appropriate solvents as described earlier and kept at room temperature until used.

The tests were conducted on unprocessed semen samples. This was to reveal the behavior of test compounds in the presence of seminal plasma as obtained results may be more representative of the natural milieu in the vagina. Ejaculate samples from 3 normospermic volunteers were collected after 2–4 days of abstinence and allowed to liquefy for 20 minutes at 37° C. The sperm count was within the range of 60–240×106 cells/ml and the percentage of motile cells was over 50%. Serial dilutions of gramicidin, nonoxynol-9, EDTA or combinations thereof were mixed with fresh semen and sperm count, motility and morphology were assessed using computer-assisted semen analysis (CASA). Each 50 mcl sample of semen was mixed in a glass tube with predetermined concentration of test compounds, vortexed for 10 seconds, and left at room temperature for 2 minutes. Thereupon, a small 10 mcl portion of the sample was placed on a glass slide and motility of the sperm was evaluated automatically. Inhibitory effects of gramicidin, N9, and EDTA on sperm motility as evaluated by CASA are shown in Table 2.

TABLE 2

IC100 of test compounds on sperm motility as determined by CASA IC100 (mcg/ml)

| | 0% EDTA | 0.1% EDTA |
|---|---|---|
| Gramicidin | 4 | 0.01 |
| Nonoxynol-9 | 200 | 125 |
| EDTA | 5,000 | — |

Although all these compounds alone could immobilize sperm, their effective doses diverged by orders of magnitude. While gramicidin abolished sperm motility within 2 minutes at 4 mcg/ml, N9 had no effect at this dose. At least 50 and 1250 times higher doses of N9 and EDTA, respectively, were required to achieve the effect comparable to that of gramicidin. The combination of 10 ng/ml of gramicidin with 0.1% of EDTA resulted in activity that was four orders of magnitude higher than the optimal combination of N9 with EDTA. The removal of gramicidin from the incubation medium by washing sperm and resuspending in Earle's balanced salt solution with 0.036 mM pyruvate and 0.5 M glucose did not restore the sperm movement. This indicates that gramicidin has an irreversible effect on sperm motility.

Cervical Mucus Penetration Assay

This technique evaluates the effect of test compounds on an important parameter of sperm function—forward motility—which correlates strongly with fertility. Glass capillary tubes (1 mm×100 mm) were filled with freshly collected lamb cervical mucus and placed vertically into solutions with test compounds as described earlier. After 30 minutes, incubation to allow the diffusion of drugs into mucus, the mucus-containing tubes were dipped vertically into cuvettes with the semen. After 15 minutes, the sperm that moved upwards from the bottom of the capillary tube was evaluated under microscope for traveled distance and the percent of motile sperm. In this assay, gramicidin alone was more potent than N9 since no complete inhibition of penetration was observed even at the highest tested doses of the latter agent (Table 3).

TABLE 3

Inhibitory doses determined in cervical mucus penetration assay IC100 (mcg/ml)

| | 0% EDTA | 0.1% EDTA |
|---|---|---|
| Gramicidin | 3 | 0.001 |
| Nonoxynol-9 | 900* | 100 |
| EDTA | 1,200 | — |

*This value for N9 represents IC50 since no IC100 was observed even at the highest tested 1 mg/ml dose.

*This value for N9 represents IC50 since no IC100 was observed even at the highest tested 1 mg/ml dose.

Although the combination of N9 with EDTA resulted in somewhat improved activity, the presence of 1 ng/mi of gramicidin with 0.1% of EDTA completely prevented the penetration of the sperm into mucus. The effective dose of gramicidin in this assay was ten-fold lower than the concentration required to inhibit sperm motility. At the time of observation, all spermatozoa that could be found in gramicidin-pretreated mucus were immotile whereas the sperm that penetrated N9-pretreated mucus retained motility even after 1 hour of incubation.

Tetrazolium Dye Reduction (XTT) Assay

The spermatozoa from fertile donors are capable of nitroblue tetrazolium reduction in a same way as the fibroblasts in Example 1. Briefly, sperm were suspended in a 96-well plate in the presence of serial ten-fold dilutions of test compounds and each 180 mcl well received 20 mcl of XTT solution at final concentration 1 mg/ml of XTT (Sigma) with 1% w/v of PMS (Aldrich, Milwaukee, Wis.). Drug untreated spermatozoa served as positive viability references.

Lactate Dehydrogenase (LDH) Assay

The disruption of the sperm membrane by N9-like detergents such as Triton X-100 or by gramicidin S leads to release of intracellular LDH isoenzymes or membrane-associated LDH-X, and an increase in LDH activity can be measured by assaying the supernatant of sperm suspension. The increase in LDH activity can be thus used as an indicator of drug toxicity since cytosolic LDH is released upon cell lysis in the same way as 51Cr is released in radioactive assays. The assay setting is similar to XTT assay and released LDH is quantitated with commercial enzymatic assay (CytoTox96, Promega, Madison, Wis.). An ordinary plate reader was used to record visible wavelength absorbance at 490 nm. The residual LDH activity usually present in seminal plasma or in incubation medium was subtracted as blank values and the % of toxicity was determined as directed by manufacturer's instruction. This assay is very sensitive and results are obtained within 30 minutes.

These two methods, XTT and LDH, were used simultaneously on the same semen samples to determine the toxic effect of gramicidin. Both quantitative tests, measuring two independent indicators of sperm viability, indicate that gramicidin is a potent nontoxic agent with antifertility potential.

It appears from the examples presented herein that gramicidin is a potent spermostatic agent acting as an irreversible inhibitor of sperm motility. Depending on the assay, gramicidin alone was 50 to 300 times more potent than N9. While the combination of N9 with EDTA had only an additive effect, gramicidin and EDTA acted together in synergistic fashion since their combined activity on sperm motility was 12,500-fold more potent than N9/EDTA. In the cervical mucus penetration assay, the activity of the gramicidin/EDTA combination was even more pronounced. The pharmaceutically acceptable doses of N9 or N9/EDTA tested in the same assay had only marginal effect since no complete inhibition was observed even at the highest tested doses. Furthermore, the efficacy of gramicidin was not affected in the presence of seminal plasma or cervical mucus suggesting that topical contraceptives with this compound could be more effective than N9-containing spermicides.

Unlike detergents such as N9 or gramicidin S, gramicidin does not act by lysing sperm, but appears to have utility as an inhibitor of sperm motility. Gramicidin has not significantly affected sperm viability parameters. Gramicidin, being a potassium ionophore, may also negatively affect the fertility by interfering with acrosome reaction and affecting sperm interaction with zona pellucida. Since gramicidin does not affect the viability parameters this compound is unrelated to spermicides known in the prior art. This utility along with the striking phenomenon of synergistic enhancement with EDTA suggests that gramicidin is a novel agent to be used in topical contraceptive preparations either alone or in combination with chelating agents such as EDTA. The present invention has identified the optimal contraceptive formulation containing low doses of gramicidin and EDTA. This combination was unexpectedly more potent than the potency of each individual agent alone and thus represents a new invention that was not anticipated by the prior art.

While the foregoing specification teaches the principles of the present invention, with examples provided for the purpose of illustration, it will be understood that the practice of the invention may comprise all of the usual modifications and variations, as anticipated within the scope of the following claims.

What is claimed is:

1. A method for treating herpes virus in a patient comprising topically administering to a virus-affected body part of said patient an anti-viral effective amount of gramicidin.

2. The method according to claim 1 wherein said herpes virus is a herpes simplex virus type 1 or type 2.

3. The method according to claim 2 wherein said herpes virus is resistant to acyclovir or anti-HSV nucleoside drugs.

4. The method according to claim 1 wherein said herpes virus is selected from the group consisting of varicella-zoster virus (VZV), cytomegalovirus (CMV), Epstein-Barr virus (EBV), HHV-6, HHV-7, and HIV-8.

5. A method of preventing a herpes virus infection in a patient in need thereof comprising topically administering to said patient in need thereof a composition comprising an anti-viral effective amount of gramicidin.

6. The method according to claim 5 wherein said composition further includes EDTA or a pharmaceutically acceptable salt.

7. The method according to claim 5 wherein said herpes virus is selected from the group consisting of varicella-zoster virus (VzV), cytomegalovirus (CMV), Epstein-Barr virus (EBV), HHV-6, HHV-7 and HHV-8.

8. A method of preventing a herpes virus infection in a patient in need thereof, said method comprising topically exposing the vaginal cavity or rectum of said patient in need thereof to a composition comprising an anti-viral effective amount of gramnicidin.

9. The method according to claim 8 wherein said herpes virus is a herpes simplex virus type 1 or type 2.

10. The method according to claim 9 wherein said herpes virus is resistant to acyclovir or anti-HSV mucleoside drugs.

11. The method according to claim 8 wherein said herpes virus is selected from the group consisting of varicella-zoster virus (VZV), cytomegalovirus (CMV), Epstein-Barr virus (EBV), HHV-6, HHV-7 and HRV-8.

* * * * *